United States Patent [19]
Marquez et al.

[11] Patent Number: 5,238,541
[45] Date of Patent: Aug. 24, 1993

[54] PROCESS FOR PRODUCTION OF AN ETHER-RICH ADDITIVE

[75] Inventors: Marco A. Marquez, Caracas; Jose C. Gonzalez, San Antonio de Los Altos, both of Venezuela

[73] Assignee: Intevep, S.A., Caracas, Venezuela

[21] Appl. No.: 847,949

[22] Filed: Mar. 6, 1992

[51] Int. Cl.$^5$ .................. B01D 3/36; C07C 7/06; C07C 41/06
[52] U.S. Cl. ..................... 203/56; 203/63; 203/91; 208/348; 568/697; 585/864
[58] Field of Search .............. 203/63, 56, 91; 568/697, 699; 585/864; 208/348

[56] References Cited

U.S. PATENT DOCUMENTS

| | | | |
|---|---|---|---|
| 5,030,768 | 7/1991 | Chen et al. | 568/697 |
| 5,064,623 | 11/1991 | Harandi et al. | 203/DIG. 6 |
| 5,100,533 | 3/1992 | Le et al. | 568/697 |
| 5,118,873 | 6/1992 | Smith | 203/DIG. 6 |
| 5,120,868 | 6/1992 | Patrini et al. | 568/689 |
| 5,120,881 | 6/1992 | Rosenfeld et al. | 568/699 |

FOREIGN PATENT DOCUMENTS 2705538 8/1978 Fed. Rep. of Germany ...... 568/699

Primary Examiner—Wilbur Bascomb, Jr.
Attorney, Agent, or Firm—Bachman & LaPointe

[57] ABSTRACT

A process for the production of an ether-rich additive for gasoline, and more particularly, the production of TAME from light hydrocarbon streams by admixing the light hydrocarbon stream, preferably from an FCC feedstock, prior to distillation of the feedstock with an alcohol in a C$_5$ feedstock and contacting the feedstock with a catalyst under etherification process conditions.

10 Claims, 3 Drawing Sheets

PROCESS FOR PRODUCTION OF AN ETHER-RICH ADDITIVE

BACKGROUND OF THE INVENTION

The present invention relates to a process for the production of an ether-rich additive for gasoline and, more particularly, the production of ter amyl methyl ether (TAME) from FCC light hydrocarbon streams containing nitriles.

MTBE, TAME or mixtures thereof are used extensively as fuel extenders and octane value improving agents in the production of unleaded gasoline. Generally, but for the inclusion of such fuel extenders and octane value improving agents, acceptable octane values can only be obtained by varying the compounding additives in the gasoline, that is, increasing the lead content of the gasoline. The desirability of lead free gasolines is clearly recognized. Lead additives in gasolines result in the emission of pollutants in exhaust gases from internal combustion engines thereby contributing to overall environmental pollution. The employment of substitutes for lead in gasoline compounds which improve the octane value of the gasoline will lead to a cleaner burning gasoline thereby improving air quality and the overall environmental condition.

Currently, MTBE is frequently selected as the octane value improving additive over TAME due to processing considerations; however, TAME is a highly desirable octane value improving additive.

There are many processes developed in the prior art for producing MTBE (methyl t-butyl ether) and TAME (methyl t-amyl ether). Typical etherification processes are disclosed in U.S. Pat. Nos. 5,001,292; 4,925,455; 4,827,045; and 4,830,635 to Harandi et al. Other known processes include that disclosed in U.S. Pat. No. 4,025,989 to Hagan et al. For the most part, these known processes for preparing ethers as additives for gasoline comprise reacting a primary alcohol, such as methanol, with an olefin having a double bond on a tertiary carbon atom, such as, isobutylene and isoamylenes. It is known in the prior art to react the alcohol and the olefin in the presence of a catalyst. Suitable known catalysts include Lewis acids (sulfuric acid) and organic acids (alkyl and aryl sulfonic acids). A particularly suitable catalyst for these reactions are ion exchange resins in their acid form of the type marketed under the trademark "AMBERLIST 15" which is a trademark of Rohm and Haas or Bayer product K2631. While many hydrocarbon feedstocks may be used for the manufacture of MTBE and TAME it is particularly useful in the petroleum refining operation to process TAME from light hydrocarbon streams resulting from fluid catalytic cracking (FCC) refinery operations. When processing FCC hydrocarbon streams under etherification conditions to form TAME it has been found that the catalysts used in the process are rapidly poisoned, that is, the catalysts are deactivated. As the catalyst materials used in known processes are relatively expensive, the foregoing problem of catalyst deactivation leads to not only process inefficiency but also substantial increases in processing costs. None of the prior art processes, and particularly none of the U.S. Patents discussed above, deal with the aforesaid problem or suggest solutions thereto.

Naturally, it would be highly desirable to provide a process for the conversion of hydrocarbon streams, particularly light naphtha hydrocarbon streams from FCC refinery processes, to TAME which overcome the problems of catalyst poisoning as discussed above.

Accordingly, it is the principal object of the present invention to provide a process for the conversion of liquid light hydrocarbon streams to TAME in an efficient and economic manner.

It is a particular object of the present invention to provide a process as aforesaid wherein the poisoning of the catalysts used in the etherification process is inhibited.

It is a further object of the present invention to provide a process as aforesaid wherein the liquid light hydrocarbon feedstock fed to the etherification zone is pretreated for processing under etherification conditions in the presence of the catalyst.

Further objects and advantages of the present invention will appear hereinbelow.

SUMMARY OF THE INVENTION

In accordance with the present invention the foregoing objects and advantages are readily obtained.

The present invention relates to a process for the production of an ether-rich additive from light hydrocarbon feedstocks and, more particularly, from FCC light hydrocarbon feedstocks having significant concentrations of nitriles, particularly propionitrile. The liquid hydrocarbon feedstocks from FCC process facilities are admixed with an alcohol for removing nitriles during distillation so as to form a $C_5$-alcohol azeotrope feedstock prior to subjecting the feedstock to the etherification process conditions in the presence of the catalyst. The purified $C_5$-alcohol azeotrope feedstock to the etherification zone is substantially free of nitriles. It has been found in accordance with the present invention that by pretreating the light hydrocarbon feedstock as aforesaid, the rate of poisoning of the catalyst employed in the etherification process is greatly reduced thereby increasing process efficiency while at the same time decreasing processing costs.

The process of the present invention wherein the feedstock to the etherification reactor is pretreated so as to remove nitriles allows for the efficient and economical production of TAME by improving the life of the catalyst used in the etherification process.

DETAILED DESCRIPTION OF THE INVENTION

Figure 1:
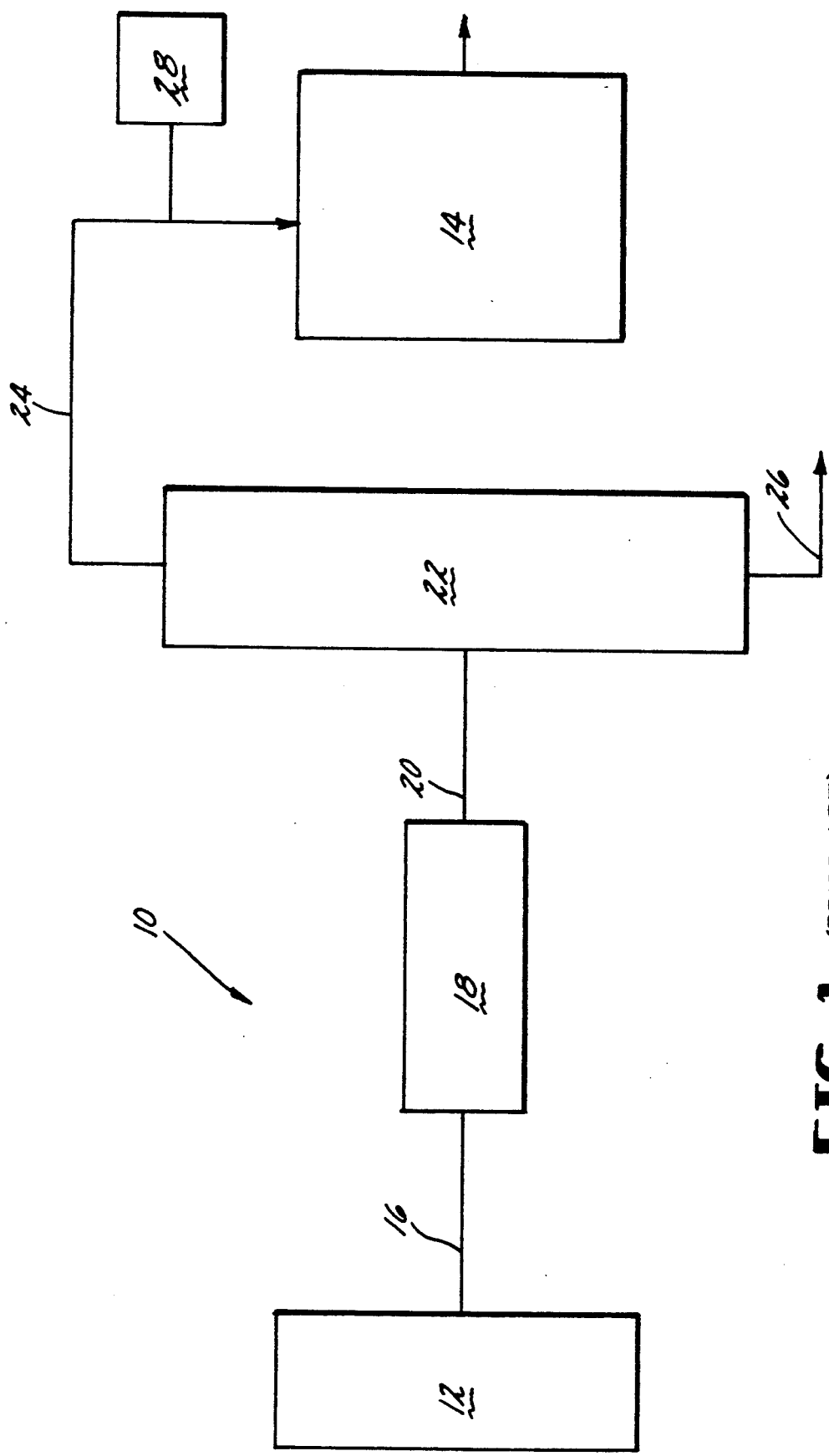
FIG. 1 is a schematic flow diagram illustrating a prior art process.

FIG. 1 is a schematic illustration of a prior art process for the production of TAME from a light hydrocarbon feedstock resulting from a fluid catalytic cracking (FCC) process. The facility 10 as illustrated in FIG. 1 comprises a FCC production facility 12 and an etherification zone 14 for converting a light hydrocarbon feedstock to an ether-rich additive, particularly, TAME. In accordance with the prior art, the light hydrocarbon feedstock from the FCC production facility 12 is delivered via conduit 16 to a unit 18 wherein any mercaptans in the hydrocarbon feedstock are oxidized in known manner. The treated product from unit 18 is thereafter passed via conduit 20 to a distillation unit 22 so as to produce a top product rich in $C_5$ for feed via line 24 to the etherification zone 14. The bottoms from the distillation unit 22 taken off line 26 are rich in $C_6+$. The ether-rich TAME product is thereafter removed from the etherification zone 14 via line 28. A typical product from the FCC refinery facility 12 which is drawn off via line 16 is characterized by the following composition: isobutene in the range of 2–7 wt. %; isoamylenes in the range of 5–10 wt. %; diolefins in the range of 1–2 wt. %; and a nitrogen concentration in the range of 22–27 ppm wherein nitriles are present in the range of 6–10 ppm. The feedstock leaving unit 18 via line 20 has a nitrile concentration in the range of 6–10 ppm. This feedstock when treated under appropriate conditions in distillation unit 22 yields an overhead product rich in $C_5$ and having a nitrile concentration in the range of between 10–14 ppm. The overhead feed from line 24 is admixed with alcohol from unit 28 and thereafter introduced into etherification zone 14 wherein it is subject to processing under the following operating conditions: pressure of between 150–300 psi, temperature of between 130°–140° F., a methanol to isoalkene ratio in the range of 1.00–1.50 moles/moles, and a ratio of $H_2$ to diolefins in the range of between 1.5 to 3.2 moles/mole. A typical catalyst used in the prior art in the etherification reaction is an acidic ion exchange resin such as the type sold under the trademark "AMBERLIST" by Rohm and Haas or Bayer prodcut K2631.

It has been found that when carrying out the process in accordance with the present invention as described above with regard to FIG. 1 that the catalyst in the etherification zone deactivates substantially over time. As a result, the efficiency of the process is reduced and the overall cost for practicing the process is increased.

Figure 2:
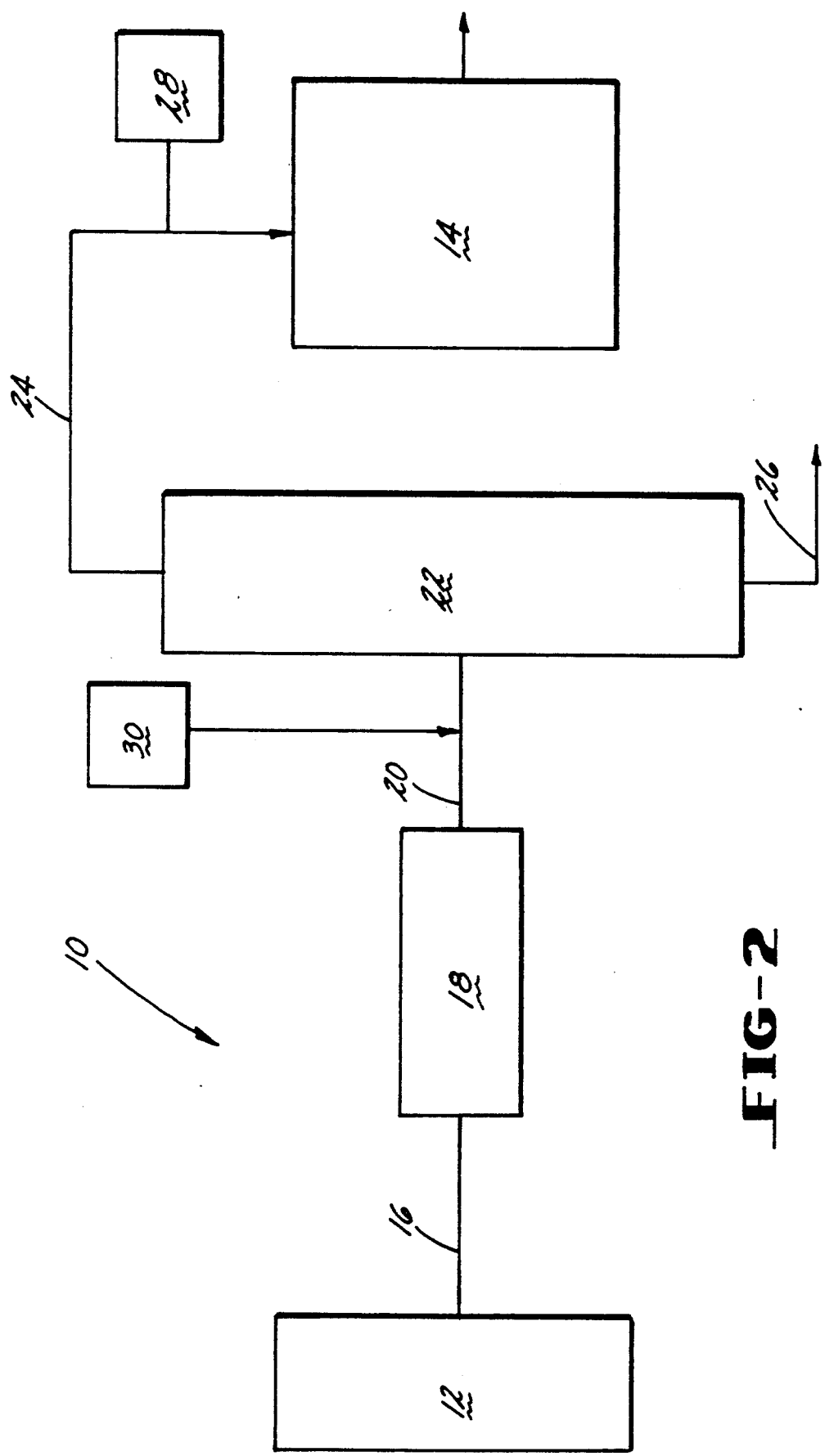
FIG. 2 is a schematic flow diagram illustrating the process of the present invention.
Figure 3:
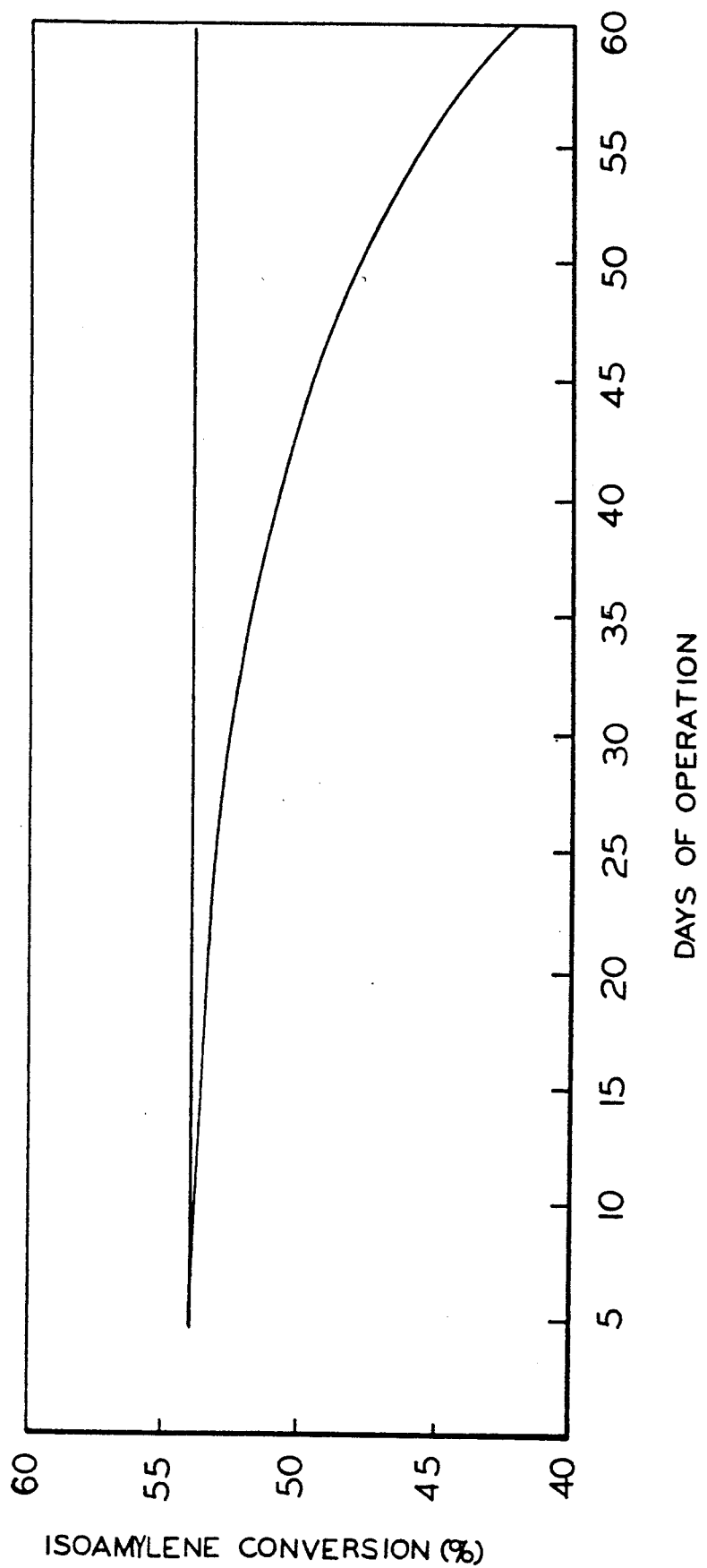
FIG. 3 is a graph demonstrating the degeneration effect of nitriles on the acid catalyst activity used in the etherification of light hydrocarbon feedstocks to TAME and the advantages of the process of the present invention.

With reference to FIG. 2, the process of the present invention which is an improvement over the above described prior art processes, is described in detail. With reference to FIG. 2, like reference numerals are employed to reference like components employed in the prior art process described in FIG. 1. Accordingly, in the process of the present invention an FCC refinery facility 12 produces a feedstock which is fed via line 16 to unit 18 wherein mercaptans within the feedstock are oxidized. The product from unit 18 is ultimately fed to distillation unit 22 via line 20 wherein the feed is distilled so as to produce an overhead feed for the etherification zone 14 via line 24 which is rich in $C_5$-alcohol azeotrope.

In accordance with the present invention a unit 30 is provided downstream of unit 18 and upstream of the distillation unit 22 for delivering a primary alcohol, particularly an alcohol selected from the group consisting of methanol, ethanol, propanol and mixtures thereof to feed line 20 for admixing the alcohol with the feedstock to the distillation unit 22. It has been found in accordance with the present invention that the $C_5$-nitriles azeotropes in the feedstock, particularly propionitriles, are broken by the presence of the alcohol introduced into the feed stream, since the $C_5$ has a great affinity for the alcohol so as to form a $C_5$-alcohol azeotripe. The feed stream is subject to distillation in the distillation unit 22. The $C_5$-alcohol azeotrope and some $C_6$-alcohol azeotrope are separated in unit 22 and fed to the etherification zone. The nitrile concentration in the feed to the etherification zone is less than or equal to 2 ppm. The remaining nitriles from the feedstock are recovered in the bottom stream 26 from the distillation unit 22.

In order to remove substantially all of the propionitriles from the feedstock in the distillation unit 22 it has been found that the amount of alcohol introduced into the feed to the distillation unit 22 in line 20 is proportional to the amount of $C_5$ in the feedstock to the distillation unit 22. It has been determined that the alcohol should be present in the final feedstock composition to the distillation unit 22 in an amount equal to at least 10 wt. % with respect to the wt. % of $C_5$ in the feedstock. For typical light hydrocarbon streams from FCC processing facilities, this amounts to an addition of between 2–4% by wt. alcohol into the feedstock for the distillation unit 22.

The $C_5$ in the feed to the distillation unit 22 have a greater affinity for the alcohol introduced into the feed line than for the propionitriles in the feed gas stream and accordingly, when the feedstock is distilled in unit 22 the $C_5$ overhead stream is substantially free of nitriles, that is, a nitrile concentration of less than or equal to 2 ppm.

The distillation tower is operated under the following conditions: pressure in the range of about 0–50 psig, temperature in the range of about 167° to about 194° F., and the ratio of isoamylenes to alcohol in the range of 0.4 to 0.6 by wt. The overhead stream substantially free of nitriles is thereafter admixed with alcohol as described above with reference to the prior art and subjected to etherification under the following conditions to produce a TAME product: pressure of between 150–300 psi, temperature of between 130°–140° F., a methanol to isoalkene ratio in the range of 1.00–1.50 moles/moles, and a ratio of $H_2$ to diolefins in the range of between 1.5 to 3.2 moles/mole.

As can be seen from the foregoing, the process of the present invention allows for the pretreatment of the feedstock to the etherification zone in an efficient manner. The advantages and superior results obtained by the process of the present invention will be made clear hereinbelow from a consideration of the following illustrative examples.

EXAMPLE I

In order to demonstrate the poisoning effect of nitriles such as propionitriles and acetonitriles on the catalyst employed in the etherification process, an untreated FCC feedstock rich in $C_5$ and having the composition set forth in Table I below was subject to etherification in the presence of an AMBERLIST ion exchange catalyst under the process and conditions set forth below in Table II. FIG. 2 shows the conversion of the feedstock to the ether-enriched product TAME over time. In order to demonstrate the benefits of pretreatment in accordance with the present invention, the same feedstock was pretreated with a methanol in an amount equal to 10 wt. % with respect to the $C_5$ content of the feedstock to obtain a purified feedstock having the concentration described below in Table I. This purified feedstock was thereafter subjected to etherification under the same process conditions set forth in Table II. The results of the effect of this feedstock on the feedstock conversion to TAME and thus the deterioration of the catalyst used in the etherification process is illustrated in FIG. 2. It can be seen from FIG. 2 that after 60 days the effectiveness on conversion of the catalyst employed in the etherification process when processing a purified feedstock treated in accordance with the present invention is substantially identical to that obtained from the virgin catalyst while the conversion effectiveness of the catalyst when processing a feedstock which was not treated in accordance with the present invention decreases substantially over time. This example clearly illustrates the effectiveness of the pretreatment of the feedstock in accordance with the present invention.

TABLE I

| FEEDING | UNTREATED | TREATED |
|---|---|---|
| Isobutene (% wt) | 8.20 | 8.00 |
| Isoamylenes (% wt) | 10.10 | 10.10 |
| Diolefins (% wt) | 0.83 | 0.77 |
| Mercaptan (ppm) | 5.00 | less than 1 |
| Nitrogen Total (ppm) | 18.00 | less than 2 |
| Nitriles (ppm) | 17.00 | less than 1 |
| Nitrogen Basic (ppm) | less than 1 | less than 1 |

TABLE II

| | |
|---|---|
| Temperature of feeding | 132 degrees F. |
| Process Pressure | 175–200 psig |
| LHSV | 2 V/V/hr |
| Ratio MeOH/ISOALKENES | 1.05 ml/ml |

EXAMPLE II

In order to demonstrate the effect of the addition of alcohol to the feedstock so as to separate nitriles from the $C_5$-$C_6$ overhead feed from a distillation unit the feedstock described in Table III below was treated in a distillation unit under the conditions set forth in Table IV. The resulting $C_5$ overhead from the distillation process were then compared for nitrile removal and the feedstock treated with the methanol was shown to have a net reduction in nitrile concentration of greater than 80%.

TABLE III

| | |
|---|---|
| $C_4$ | 4.0 wt. % |
| $C_5$ | 25.0 wt. % |
| Isoamylenes | 6.1 wt. % |
| $C_6$ | 21.0 wt. % |
| $C_6+$ | 50.0 wt. % |
| Total Nitrogen | 25.6 ppm |
| Nitriles: | |
| Acetonitrile | 1.7 ppm |
| Propionitrile | 5.4 ppm |

TABLE IV

| | |
|---|---|
| Feeding Temperature | 45° C. |
| Feeding Plate | 30 |
| Condenser Water Temp. | 0° C. |
| Reboiler Temp. | 75° C. |
| Feeding Flow | 8 L/H |
| Methanol Quantity | 3.00 wt. % to feeding |

As can be seen from the foregoing, the process of the present invention provides for an effective and economical process for producing ether-rich additives such as TAME and MTBE from light hydrocarbon feedstocks.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A process for the production of tertiary amyl methyl ether (TAME) comprising:
    (a) providing a liquid hydrocarbon $C_4$-$C_{12}$ feedstock containing nitriles and isoamylenes;
    (b) admixing said liquid hydrocarbon $C_4$-$C_{12}$ feedstock with an alcohol selected from the group consisting of methanol, ethanol, propanol and mixtures thereof to form a mixture of hydrocarbon feedstock and alcohol;
    (c) distilling said mixture of hydrocarbon feedstock and alcohol under controlled conditions so as to obtain a product comprising a $C_5$ hydrocarbon-alcohol azeotrope feedstock rich in $C_5$ and substantially free of nitriles; and
    (d) contacting said $C_5$ hydrocarbon-alcohol azeotrope with a catalyst under etherification process conditions to produce tertiary amyl methyl ether (TAME).

2. A process according to claim 1 wherein the mixture of hydrocarbon feedstock and alcohol is distilled in a distillation tower.

3. A process according to claim 2 wherein the distillation tower is operated under the following conditions: pressure in the range of about 0–50 psig, temperature in the range of about 167° to about 194° F., and the ratio of isoamylenes to alcohol in the range of 0.4 to 0.6 by wt.

4. The process according to claim 1 wherein the feedstock is FCC naphtha hydrocarbon feedstock.

5. The process according to claim 1 wherein the nitriles include propionitrile.

6. The process according to claim 4 wherein the FCC naphtha hydrocarbon feedstock is a cut rich in $C_5$.

7. The process according to claim 1 wherein the catalyst is an acidic etherification catalyst in the form of an ion exchange resin.

8. The process according to claim 2 wherein the liquid hydrocarbon feedstock to the distillation tower is admixed with said alcohol in an amount of about between 2.0 to about 4.0 wt. % with respect to the liquid hydrocarbon feedstock.

9. The process according to claim 1 wherein the alcohol is methanol.

10. The process according to claim 1 wherein the $C_5$ hydrocarbon-alcohol azeotrope feedstock has total nitrile content in the range of about 0 to about 2 ppm.

* * * * *

Adverse Decisions in Interference

Patent No. 5,238,541, Marco A. Marquez, Jose C. Gonzalez, PROCESS FOR PRODUCTION OF AN ETHER-RICH ADDITIVE, Interference No. 103,668, final judgment adverse to patentees rendered October 15, 1997, as to claims 1-10.

*(Official Gazette April 21, 1998)*